(12) United States Patent
Hart et al.

(10) Patent No.: US 6,579,304 B1
(45) Date of Patent: Jun. 17, 2003

(54) SURGICAL CLAMP WITH IMPROVED TRACTION

(75) Inventors: Charles C. Hart, Huntington Beach, CA (US); Haruyasu Yawata, Huntington Beach, CA (US); Robert Fishburn, Huntington Beach, CA (US); Donald L. Gadberry, Dana Point, CA (US); Eduardo Chi-Sing, Laguna Niguel, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 0 days.

(21) Appl. No.: 08/923,211

(22) Filed: Sep. 4, 1997

Related U.S. Application Data

(60) Provisional application No. 60/037,077, filed on Feb. 3, 1997.

(51) Int. Cl.[7] ............................................. A61B 17/28
(52) U.S. Cl. ...................... 606/207; 606/157; 606/205
(58) Field of Search ............................ 606/1, 205–211, 606/174, 50–52, 151–158, 107, 139–148; 81/300–427.5; 294/87.22–87.28, 99.1–100, 103.1–119.4

(56) References Cited

U.S. PATENT DOCUMENTS

| | | | |
|---|---|---|---|
| 2,723,666 A | * | 11/1955 | Greenberg .................. 606/205 |
| 3,503,396 A | * | 3/1970 | Pierie et al. ................. 606/207 |
| 3,503,397 A | | 3/1970 | Fogarty et al. |
| 3,503,398 A | | 3/1970 | Fogarty et al. |
| 3,515,139 A | | 6/1970 | Mallina |
| 3,726,279 A | | 4/1973 | Barefoot et al. |
| 3,746,002 A | | 7/1973 | Haller |
| 4,120,302 A | | 10/1978 | Ziegler |
| 4,578,080 A | | 3/1986 | Helal ............................ 623/13 |
| 4,821,719 A | | 4/1989 | Fogarty ....................... 128/325 |
| 5,027,482 A | * | 7/1991 | Torppey ........................ 24/306 |
| 5,171,253 A | | 12/1992 | Klieman ...................... 606/158 |
| 5,250,072 A | | 10/1993 | Jain ............................. 606/205 |
| 5,372,596 A | | 12/1994 | Klicek et al. .................. 606/35 |
| 5,549,627 A | | 8/1996 | Kieturakis ................... 606/206 |
| 5,591,182 A | | 1/1997 | Johnson ...................... 606/151 |
| 5,674,237 A | | 10/1997 | Ott .............................. 606/185 |
| 5,681,336 A | | 10/1997 | Clement et al. ............. 606/159 |

FOREIGN PATENT DOCUMENTS

| | | | | |
|---|---|---|---|---|
| JP | 57154407 | * | 9/1982 | ................. 264/561 |
| RU | 668675 | | 7/1979 | |

* cited by examiner

*Primary Examiner*—Glenn K. Dawson
(74) *Attorney, Agent, or Firm*—Richard L. Myers

(57) ABSTRACT

A surgical clamp includes opposing jaws and a covering enhancing traction between the jaws and a body conduit. A multiplicity of fibers oriented to extend longitudinally between the clamp and conduit may be composed of filaments and either woven or non-woven to form a fabric. A variety of weaves are contemplated to provide different textures, each having its own traction characteristics. The nature of the weave can control characteristics such as smoothness, absorption, and texture. The fibers or filaments may be formed from any solid or semi-solid material, adding its own characteristics to the resulting fabric insert or clamp.

34 Claims, 7 Drawing Sheets

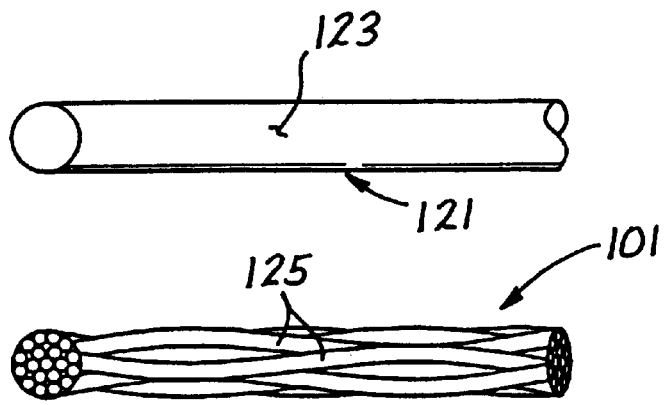
FIG. 20
FIG. 21
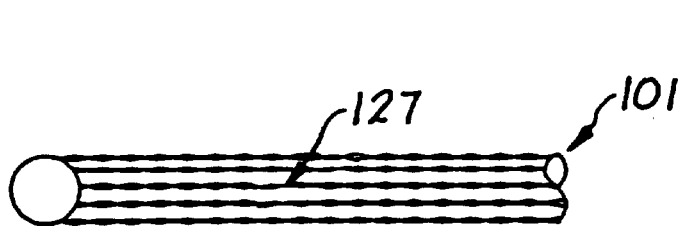
FIG. 22
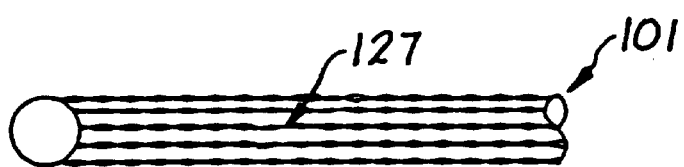
FIG. 23
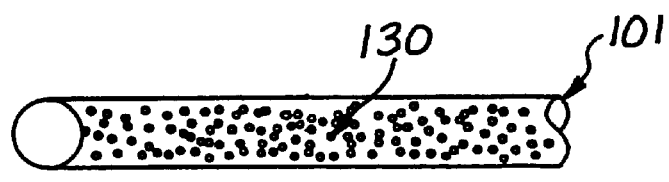
FIG. 24
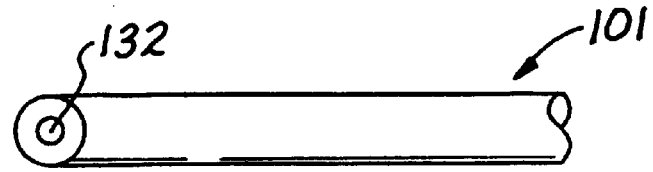
FIG. 25
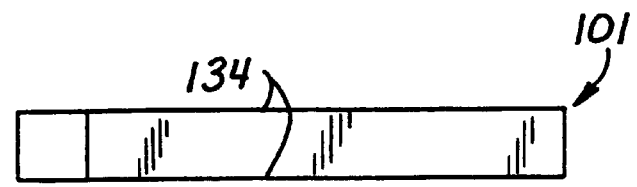
FIG. 26
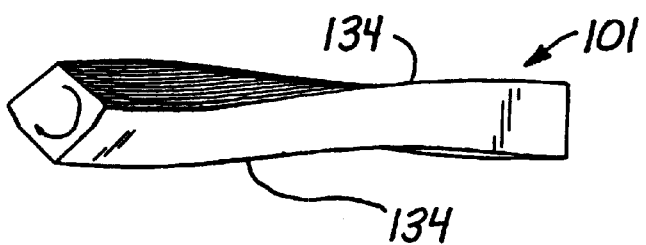

SURGICAL CLAMP WITH IMPROVED TRACTION

CROSS-REFERENCE TO RELATED APPLICATIONS

This application is a non-provisional application based on provisional application serial No. 60/037,077, filed on Feb. 3, 1997, and entitled "Surgical Instruments with Improved Traction".

FIELD OF THE INVENTION

This invention relates generally to surgical conduit occlusion devices such as clips and clamps, and more specifically to tissue contacting surfaces commonly associated with inserts for clips and clamps.

Discussion of the Prior Art

The human body contains many body conduits which accommodate a flow of fluids or semi-solids among various locations of the body. Typical of such conduits are the intestines, and, in particular, the blood vessels including both veins and arteries.

Many surgical procedures require the reduction of flow, and more typically, the occlusion of flow in such body conduits. This occlusion is typically accomplished with devices commonly referred to as clamps or clips. In general, these devices have opposing jaws which are adapted to extend exteriorly over the body conduit and to pinch the walls of the conduit against themselves in order to inhibit or stop flow through the conduit.

The jaws commonly associated with clamps are relatively long and are operable by scissor-type handles which provide leverage for the jaws. Clamps are commonly used to occlude larger conduits such as the intestines. By comparison, the jaws of clips are relatively small and are biased by a spring contained in a telescoping housing. The smaller clips are commonly used to occlude smaller conduits such as vessels. As used herein, the word "clamp" will refer not only to clips and clamps but other types of occlusion devices which have opposing jaws.

Body conduits typically have a relatively smooth outer surface which is often wetted by body fluids such as blood. Attempts to occlude such conduits by exteriorally pinching their walls must meet two objectives. Of course, the first objective is to accomplish the occlusion. But of no less importance is the second objective, to maintain the clamp in place. Herein lies the problem commonly referred to as traction.

Traction in this case relates to the resistance of the clamp to movement relative to the tissue. Theoretically, this traction is equivalent to the product of a coefficient of friction, which is dependent upon the nature of the contacting surfaces, and the normal or clamping force. In the past, attempts have been made to increase this clamping force in order to increase the traction. Unfortunately, squeezing the body conduit with a greater force tends to traumatize the tissue and in the case of vessels, destroy the precious intimal lining which cannot be regenerated. As a result, it is desirable to have only sufficient clamping force to achieve the first objective, that is, the occlusion of the conduit. Increasing the clamping force to achieve the second objective, that is, increase traction, is generally not a suitable alternative.

Attempts have been made to increase the coefficient of friction in order to enhance the traction of the clamp relative to the conduit. This has been complicated by the wetness of the tissue surface of the conduit. U.S. Pat. No. 3,746,002 discloses an Atraumatic Surgical Clamp having a plurality of pin members which extend through a resilient pad and engage the tissue when the pad is compressed. Since the pins stick into the tissue, this produces a highly traumatic effect in most cases. Less heroic attempts to increase the coefficient of friction have not always been sufficient to maintain the clamp in place, even after the conduit has been occluded.

Resilient pads, commonly referred to as inserts, have been provided for attachment to the inner surfaces of the opposing jaws. These inserts typically have a tissue-contacting surface which faces the opposing jaw, as well as a pair of side-surfaces that extend laterally of the insert. Various systems for attaching the inserts to the jaws of the clamp are well-known to those skilled in the art.

In an effort to increase the traction of the inserts, they have been formed of resilient foam and, in some cases, molded with irregular surfaces. In other cases, fibers have been placed along the tissue-contacting surface of the insert in an upstanding relationship similar to the bristles of a toothbrush. Where the ends of these fibers have contacted the conduit, traction has been good, but attempts to increase the occlusion pressure has typically caused the fibers to bend so that only the sides of the fibers remain in contact with the conduit. This generally reduces the coefficient of friction and therefore promotes slippage. Furthermore, fibers have only been placed along the tissue-contacting surface of the insert. Where the insert has been compressed, the resilient pad has expanded bringing the side surfaces into contact with the conduit. Unfortunately, this has not increased contact with the upstanding fibers since these have been limited only to the tissue-contacting surface. Typical of this art is the disclosure in U.S. Pat. No. 4,821,719, issued on Apr. 18, 1989, and entitled "Cohesive-Adhesive Atraumatic Clamp."

SUMMARY OF INVENTION

These deficiencies of the prior art are overcome with the many embodiments of the present invention which provide increased traction between a clamp and body conduit. This traction is provided in several cases by a multiplicity of fibers oriented in their natural state to extend longitudinally between the clamp and conduit. These fibers, which may themselves be composed of filaments, can be woven or non-woven into a fabric for covering a resilient pad or clamp insert. All forms of weaves are contemplated, each providing a texture which may be of particular advantage in different procedures. The nature of the weave may control characteristics such as smoothness, absorption, and texture. The fibers and filaments may be formed from any solid or semi-solid material, each material adding its own characteristics to the resulting fabric insert or clamp.

Providing this traction-enhancing covering over the sides of the insert brings additional traction-enhancing surface into contact with the conduit as the insert is compressed.

The invention comtemplates not only variations in the weave or structure of the fabric forming the covering, but also the structure of each filament or fiber which may contribute to that fabric. Forming the fabric of specific materials or providing those materials in a covering for the fabric or filaments can also improve traction characteristics.

In one aspect of the invention, a surgical instrument for clamping a body conduit to includes first and second opposing jaws and at least one insert. An insert carried by one of the jaws includes a first layer formed of a first material having first-traction characteristics with a body conduit, the first layer being defined in a natural state by an opposing surface and a pair of side-surfaces. A second layer of the insert is formed of a second material having second-traction characteristics greater than the first-traction characteristics. This second layer extends at least partially over the opposing surface and the side surfaces of the first layer and provides a first area of contact with the conduit when the insert is in the natural state and a second area of contact when the insert is in the compressed state. This construction adds the improved traction of the second layer to the increased area of contract provided by the insert in the compressed state. In another aspect of the invention, a surgical clamp includes first and second opposing jaws. A first layer carried by the first jaw has first-compliant characteristics and first-traction characteristics. A second layer carried by the first jaw in juxtaposition to the first layer has second-complaint characteristics and second-traction characteristics. The second-complaint characteristics of the second layer are less than the first-compliant characteristics of the first layer, and the second-traction characteristics of the second layer are greater than the first-traction characteristics of the first layer. A multiplicity of fibers are included in this second layer and oriented generally in a common plane. In an additional aspect of the present invention, the multiplicity of fibers included in the second layer have an elongate configuration and a side-surface extending longitudinally between a first end and a second end. This side-surface of at least one of the fibers is uneven in order to provide the second layer with improved traction relative to the body conduit.

In a further aspect of the invention, at least one jaw of a surgical clamp is provided with an outer fabric which is defined at least in part by a tissue-contacting surface. This fabric will typically be formed of a multiplicity of fibers that are disposed generally in a planer orientation. The fibers may be arranged in a random order or woven. The weave may be conventional or may include any one of the other well-known weave constructions.

These and other features and advantages of the present invention will be more apparent with a description of preferred embodiments in reference to the associated drawings.

DESCRIPTION OF THE DRAWINGS

FIG. 20 is a side-elevation view illustrating a monofilament associated with the present invention;

FIG. 21 is a side-elevation view of a fiber including multiple filaments;

FIG. 22 is a side-elevation view of a filament having an irregular surface;

FIG. 23 is a side-elevation view of a filament formed of sponge;

FIG. 24 is a side-elevation view of a hollow filament;

FIG. 25 is a side-elevation view of a filament having a polygonal cross-section; and FIG. 26 is a side-elevation view of a filament of FIG. 25 twisted along its longitudinal axis.

DESCRIPTION OF PREFERRED EMBODIMENTS

Figure 1:
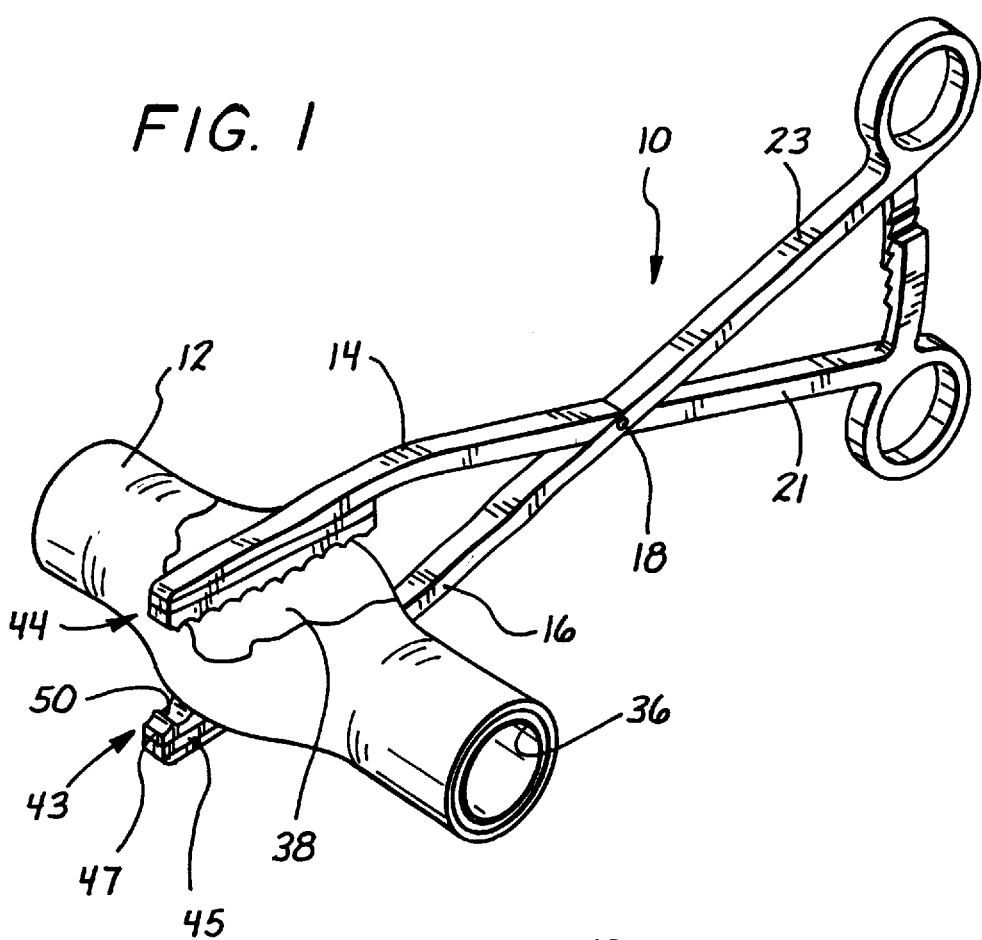
FIG. 1 is a perspective view of a surgical clamp of the present invention engaging a body conduit.

Clamps are commonly used to restrict the flow of fluids and semi-solids in body conduits. By way of example, a clamp 10 is illustrated in FIG. 1 and designated generally by the reference numeral 10. This clamp is illustrated in an operative state occluding a body conduit such as a portion of an intestine 12. The clamp 10 has a pair of opposing jaws 14 and 16 which are pivotal relative to each other at a fulcrum 18 by operation of associated scissor-type handles 21 and 23, respectively. Since the intestine 12 is a relatively large conduit, the clamp 10 will typically have jaws 14, 16 with a length of about two-to-three inches.

Figure 2:
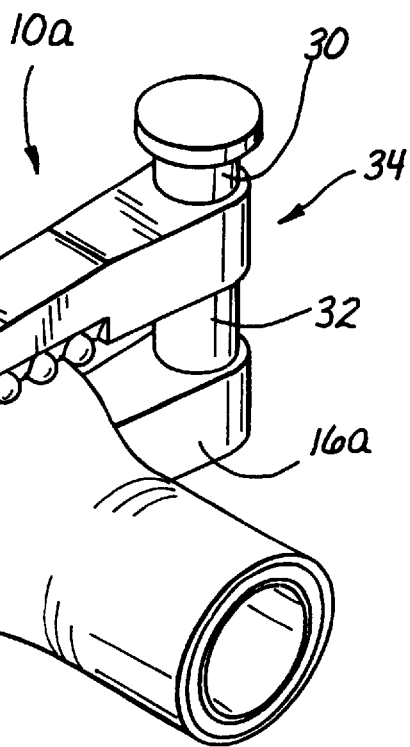
FIG. 2 is a perspective view of a surgical clip of the present invention engaging the body conduit.

Another type of clamp is illustrated in FIG. 2, wherein elements of structures similar to those previously discussed or designated by the same reference numeral followed by the lower case letter "a". Thus, the clamp 10a in FIG. 2 has a pair of opposing jaws 14a and 16a, which may have a length less than about one inch. Thus, the clamp 10a is more specifically adapted to occlude smaller body conduits such as a blood vessel 12a. In the illustrated embodiment, the jaws 14a, 16a are coupled to telescoping portions 30 and 32, respectively, of a barrel 34. One or both of these barrel portions 30, 32 may be hollow in order to house a spring (not shown) which is adapted to bias the jaws 14a, 16a into a closed position. The clamp 10a is commonly referred to as a clip, but has clamping characteristics similar to those of the clamp 10 illustrated in FIG. 1. Accordingly, the word "clamp" will hereinafter refer to any occlusion device having opposing jaws, such as the jaws 14 and 16, which are moveable between an open state and a closed state. The jaws 14, 16 in the open state are widely separated to facilitate insertion of the associated conduit 12 between the jaws. In the closed state, the jaws 14, 16 are closely spaced to engage the exterior of the conduit 12, and to pinch opposing walls of the conduit 12 against themselves so as to create a restriction in the flow of fluids through the conduit 12.

This restriction may result in total occlusion of the conduit 12 if the opposing walls are pinched into contact by the jaws 14, 16 of the clamp 10. Where complete occlusion is desired, substantial clamping forces may be required in order to bring the opposing walls of the conduit 12 into contact. These forces, of course, tend to traumatize the conduit 12 and, importantly in the case of vessels, may damage the inner, intimal lining 36 of the vessel. Since this intimal lining 36 cannot be regenerated, substantial occlusion forces are to be avoided.

While it can be appreciated that reduced clamping forces may be desirable to inhibit trauma to the conduit 12, increased clamping forces may be desirable to facilitate traction with the conduit 12 in order to maintain the clamp 10 in its occlusive state. Traction can be a difficult problem particularly in a surgical environment wherein the outer surface of the conduit 12 will typically be wetted or coated with a liquid such as blood 38.

It is for these reasons that the clamp 10 is designed to address competing requirements for a clamping force reduced to avoid trauma to the conduit 12, and a sheer force increased to facilitate traction between the clamp 10 and the conduit 12.

In the past, trauma has been addressed by providing resilient pads or inserts 41 and 43, one for each of the associated jaws 14 and 16. The inserts 41 and 43 have commonly included rubber or foam which has provided a relatively soft tissue-contacting surface for the jaws 14, 16. In some cases, this tissue-contacting, surface has been molded with an irregular shape facilitating traction with the conduit 12. Shapes of particular interest are disclosed by applicant in U.S. provisional application, serial No. 60/037, 077, filed on Feb. 3, 1997, and entitled "Surgical Instruments with Improved Traction".

The insert 43 has a generally rigid, such as plastic, substrate or base 45 which is coupled to the associated jaw 16. A resilient pad 47 is attached to the base 45 and overlaid with a cover 50, of particular advantage to the present invention. It is this cover 50, with or without the resilient pad 47, which provides increased traction without an increase in clamping force or a resulting increase in trauma to the conduit 12.

The clamp 10 will typically include reusable jaws 14, 16 in combination with disposable inserts 41, 43. However, the concept of this invention is equally applicable to clamps having jaws with non-removable tissue-contacting elements.

Figure 3:
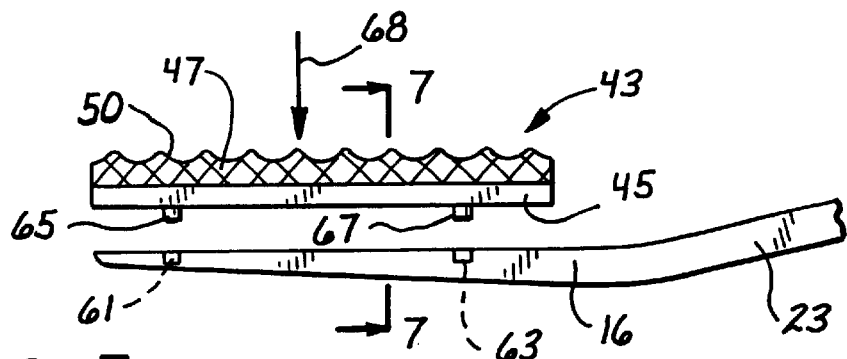
FIG. 3 is a side-elevation view of a clamp jaw and system for attaching a disposable insert of the present invention.

In an embodiment including disposable inserts, attachment of the jaws 16 to the insert 43 can be accomplished with a variety of systems. Typically, the jaw 16 will include a top surface 52 facing toward to the opposing jaw 14, an opposing bottom surface 54, and a pair of side-surfaces 56 extending therebetween. In the embodiment of FIG. 3, the top surface 52 is provided with a pair of holes 61, 63, which are sized and configured to receive complementary projections 65, 67 on the base 45 of the insert 43. In a preferred embodiment, the projections 65, 67 and associated holes 61, 63 have a snap fit relationship facilitating removable attachment of the insert 43 to the jaw 16. In the FIG. 3 embodiment, the insert 43 is mounted by moving the base 45 downwardly onto the jaws 16 generally along arrow 68.

Figure 4:
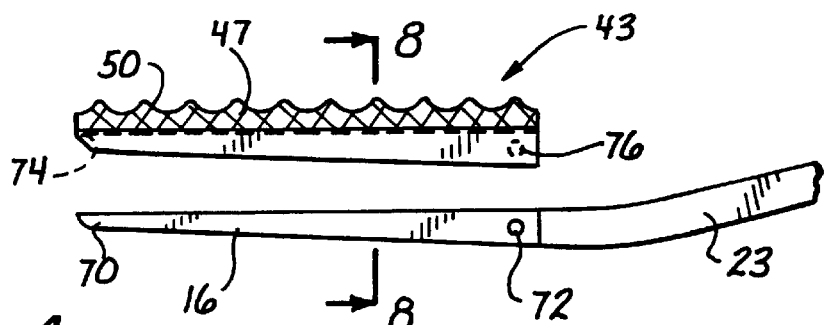
FIG. 4 is a side-elevation view of a clamp jaw and system for attachment of a further embodiment of a disposable insert.
Figure 5:
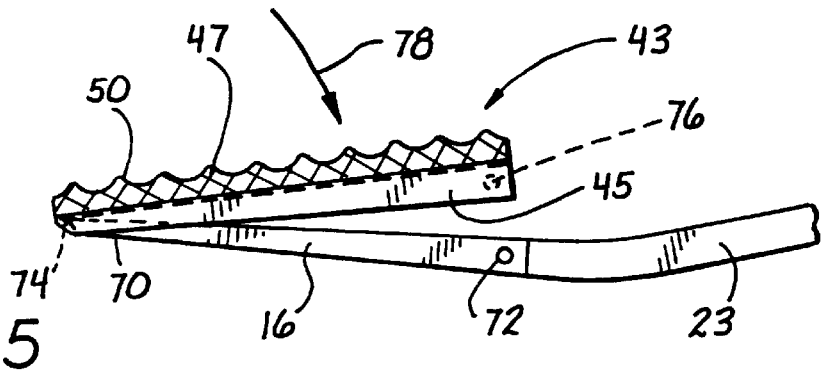
FIG. 5 is a side-elevation view illustrating attachment of the insert illustrated in FIG. 4.

In the embodiment of FIG. 4, a lip 70 is provided at the distal end of the jaw 16 and a recess 72 provided along the side surface 56. The associated insert 43 has a base 45 which is configured with an undercut 74 sized to receive the lip 70, and at least one projection 76 which combines with the recess 72 in a snap-fit relationship. In this case, the insert 43 is mounted by engaging the undercut 74 with the distal lip 70 and then tilting the insert 43 generally in the direction of arrow 78 until the projection 76 snaps into the recess 72, as illustrated in FIG. 5.

Figure 6:
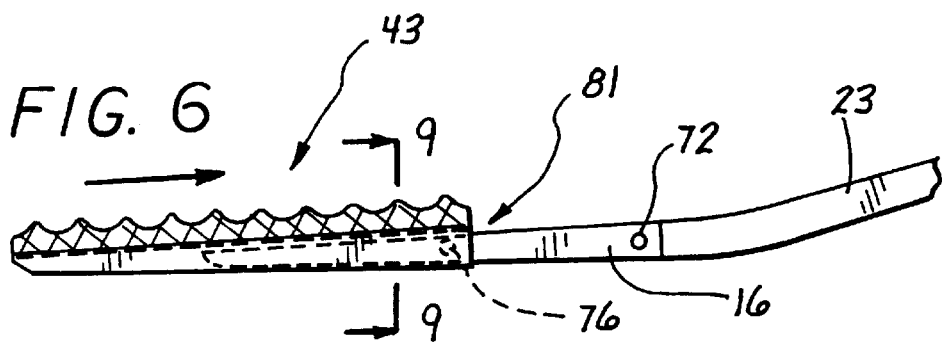
FIG. 6 is a side-elevation view of a further embodiment of an insert illustrating a preferred method of attachment.

In still a further embodiment illustrated in FIG. 6, the insert 43 is provided with a tubular construction including a central channel 81 which is sized and configured to receive the tapered jaw 16. In this embodiment, the tubular insert 43 is mounted by inserting the jaws 16 into the channel 81 and moving the insert 43 relative to the jaw 16 until the projection 76 registers with the recess 72.

Figure 7:
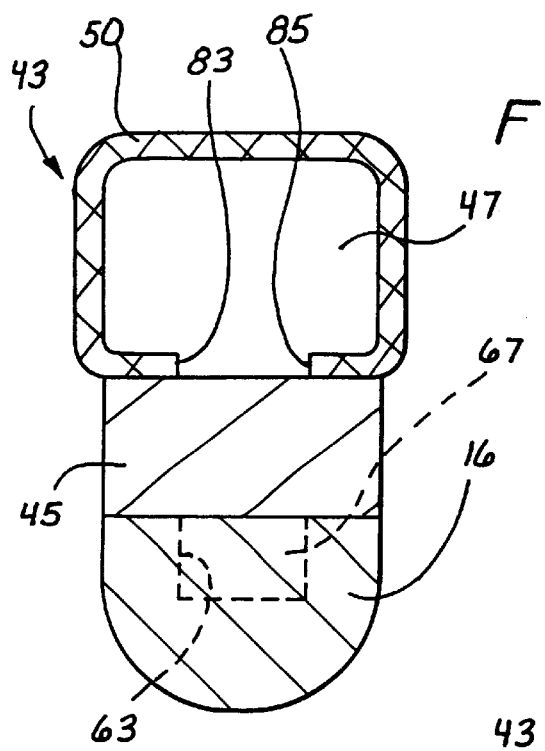
FIG. 7 is a cross-section view taken along lines 7—7 of FIG. 3.
Figure 8:
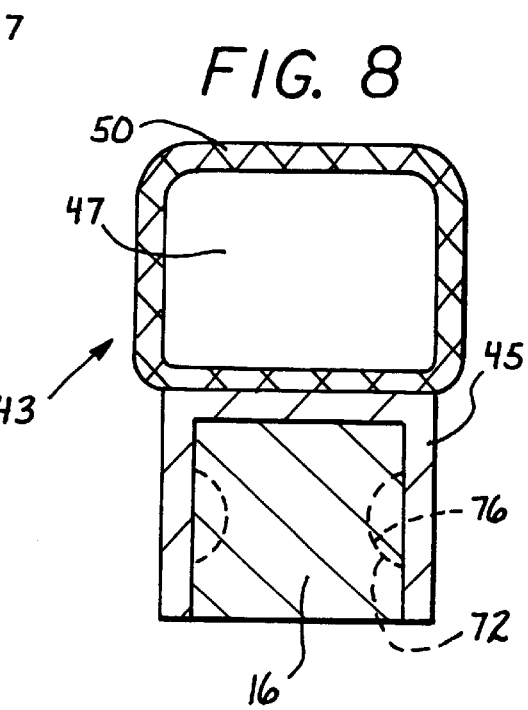
FIG. 8 is a cross-section view taken along lines 8—8 of FIG. 4.
Figure 9:
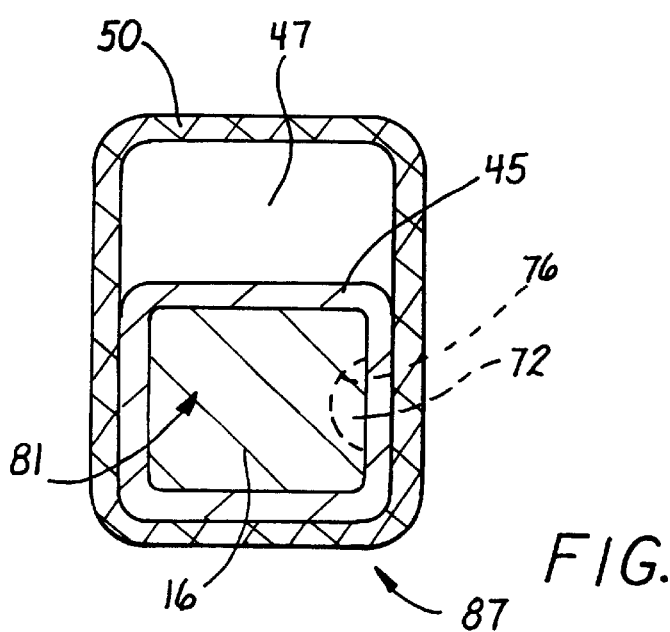
FIG. 9 is a cross-section view taken along lines 9—9 of FIG. 6.

A cross-sectional view of each of the embodiments illustrated in FIGS. 3, 4, and 6 is provided in FIGS. 7, 8, and 9, respectively. These views are of additional interest because they show different constructions including the cover 15. In the embodiment of FIGS. 3 and 7, the cover 50 is generally rectangular in shape with long edges 83 and 85, which are folded over the pad 47 and brought into a general abutting relationship between the pad 47 and the base 45. In such an embodiment, the cover 50 could also be configured to extend around both the base 45 and the pad 47.

In the embodiment of FIGS. 4 and 8, the cover 50 is a tubular structure and extends entirely around the resilient pad 47. In the embodiment of FIGS. 6 and 9, the tubular cover 50 extends around both the base 45 and pad 47. In this case, the base 45 is also provided with a tubular structure in order to form the channel 81. This particular embodiment offers further advantages in that the added traction provided by the cover 50 is also present on the back-side or bottom of the jaw 16, as shown generally by arrow 87. Increased traction along this surface will enable the surgeon to engage tissue with the back-side of the clamp 10 and push that tissue to a desired location.

Figure 10:
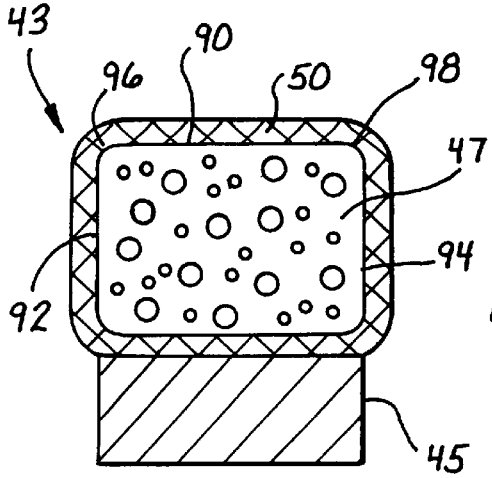
FIG. 10 is a cross-section view similar to those of FIGS. 7–9 and illustrating an additional embodiment of the present invention.
Figure 11:
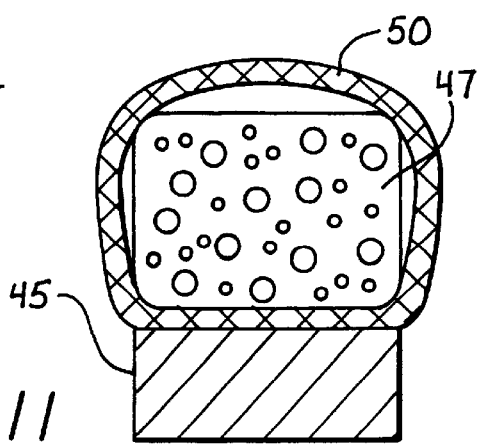
FIG. 11 is a cross-section view similar to those of FIGS. 7–9 and illustrating a further embodiment of the present invention.

In all of these embodiments, the relationship of the resilient pad 47 to the surrounding cover 50 can also be varied to provide different traction characteristics to the insert 43. For example, as illustrated in FIG. 10, the cover 50 can be drawn tightly against the surface of the pad 47 so that substantially no movement can occur between the cover 50 and pad 47. By comparison, the cover 50 in the embodiment of FIG. 11 is formed loosely around the pad 47 so that some movement between the cover 50 and pad 47 can occur. Since the cover 50 is less embedded in the pad 47 in the FIG. 11 embodiment, traction tends to be greater for this construction.

Figure 12:
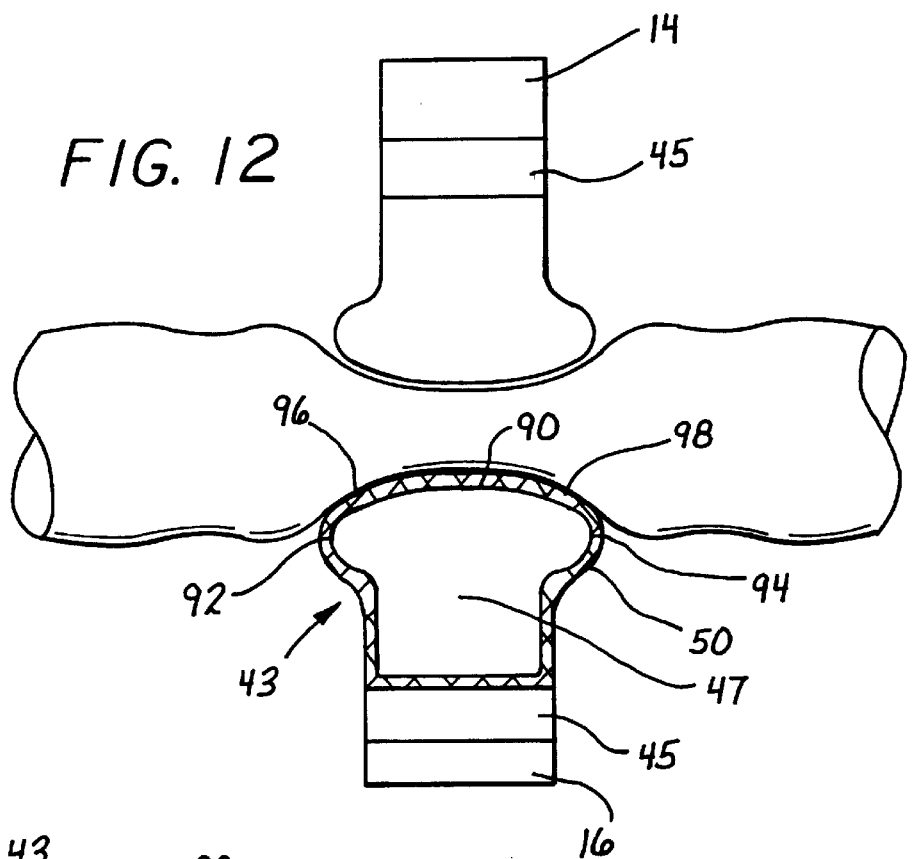
FIG. 12 is a planned view illustrating opposing jaws and an increased area of contact with a traction-enhancing insert cover.

Another significant feature associated with the present invention can best be understood with reference to FIGS. 10 and 12. In FIG. 10, the insert 43 is shown in a natural, uncompressed state. In FIG. 12, the same insert is shown operatively applied to the conduit 12 in a compressed state. With reference to FIG. 10 it can be seen that the resilient pad 47 includes an upper or tissue-facing surface 90 and a pair of side-surfaces 92 and 94. In the natural state, the top surface 90 intersects with each of the side-surfaces 92 and 94 at respective points of intersection designated by the reference numerals 96 and 98. In the constructions of the past, traction-enhancing structures are formed on the top-surface 90 but not on the side-surfaces 92 and 94. As a consequence, when a compressive pressure is applied to the insert 43, as illustrated in FIG. 12, there is no increase in the area between the traction-enhancing structure and the associated conduit 12.

With the present invention, it will be noted that the cover 50 extends over not only the top surface 90 but also the side-surfaces 92 and 94. In the compressed state illustrated in FIG. 12, the side-surfaces 92, 94 spread to provide additional area of contact between the cover 50 and the conduit 12. Note in FIG. 12 that the points of intersection 96 and 98 are disposed within this area of contact when the insert 43 is in the compressed state. Increasing this area of contact in the compressed state operates to increase the advantageous characteristics associated with the cover 50. Thus, as additional clamping pressure is applied and the resilient pad 47 spreads, the advantageous traction characteristics associated with the cover 50 are increased. Providing these traction-enhancing characteristics along the side of the insert 43 can be of particular advantage in certain embodiments of the invention.

Figure 14:
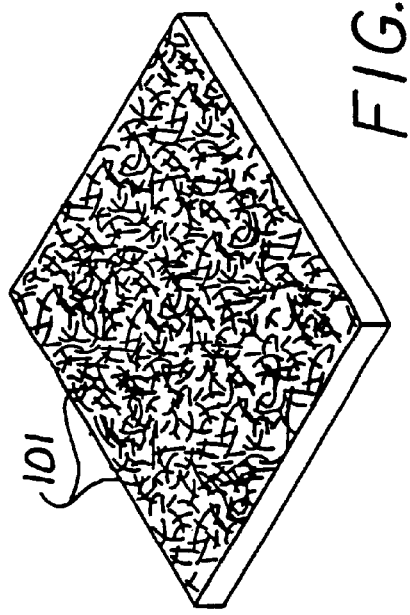
FIG. 14 is a perspective view of a non-woven fabric associated with the present invention.
Figure 13:
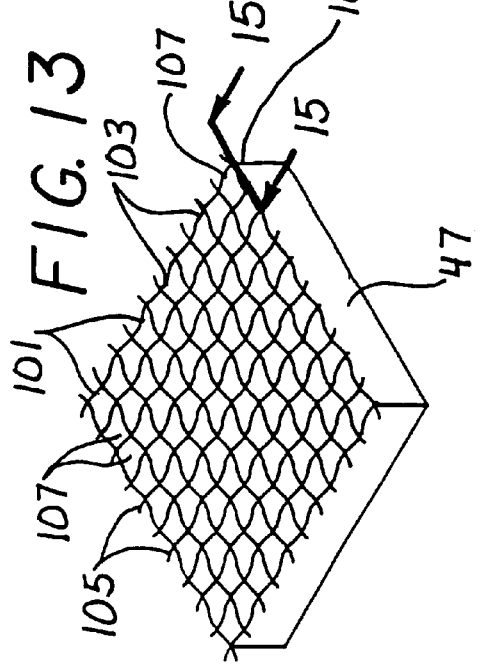
FIG. 13 is a perspective view of a weave associated with a fabric cover of the present invention.

Turning now to the characteristics of the cover 50, it will be apparent that traction can be improved when the cover 50 includes a multiplicity of elongate fibers 101 oriented to extend generally in a plane which is parallel to the jaws 14, 16. With this orientation, fibers 101 are positioned generally with the elongate side of each fiber facing the tissue to be contacted, such as the conduit 12. The fibers 101 may be arranged in sets wherein each of the fibers in the set extends in a common direction. With reference to FIG. 13, it will be noted that the fibers 101 are arranged in a set 103 which includes generally parallel fibers which extend upwardly to the right, and a set 105 which includes generally parallel fibers which extend upwardly to the left. Alternatively, the fibers 101 may be disposed in a random configuration as illustrated in FIG. 14. The fibers 101 may be relatively long so that they extend entirely across the cover 50, as illustrated in FIG. 13, or relatively short, as illustrated in FIG. 14. In some cases, the fibers 101 will form a piece of sheet material or fabric 106 which may be woven as illustrated in FIG. 13, or non-woven as illustrated in FIG. 14. In the case of a non-woven sheet material, the cover 50 may comprise a felt, a mat, or a material sometimes referred to as roven or felt.

Figure 15:
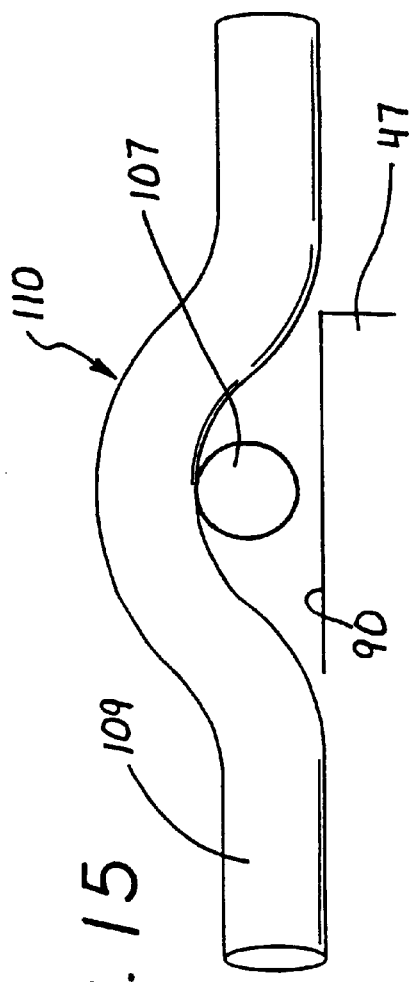
FIG. 15 is a cross-section view taken along lines 15—15 of FIG. 13.

The surprising traction afforded by the cover 50 is believed to result from the irregular surface which is brought into contact with the tissue, such as the conduit 12. This can be better understood with reference to FIGS. 13 and 15, which illustrate a pair of intersecting fibers 107 and 109. These fibers, as well as all of the fibers 101, define openings or interstices 110 through which the tissue 12 is exposed to the top surface 90 associated with the pad 47. Where the tissue 12 is exposed to only a single fiber, such as the fiber 107, a different level of texture is presented to the tissue 12. This level extends above the surface 90 an amount generally equivalent to the diameter of the fiber 107. At those points where fibers 101 intersect, such as where the fiber 107 and the fiber 109 intersect in FIG. 15, a third level of texture is presented to the tissue 12. This level extends above the surface 90 a distance generally equivalent to the diameter of the fiber 107 plus the diameter of the fiber 109. With these different levels of texture pressing into the tissue, such as the conduit 12, a high degree of traction results without any increase in trauma to the tissue.

Figure 16:
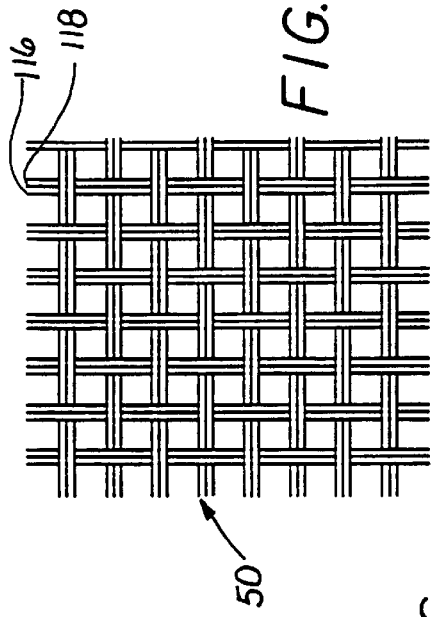
FIG. 16 illustrates a conventional weave associated with the present invention.

Realizing that it is this irregular or aggravated texture which is provided for contacting the tissue, it should now be apparent that each type of weave in the prior art will present different characteristics which may offer particular advantages in various embodiments of the invention. For example, a fabric might be woven in a conventional weave, such as that illustrated in FIG. 16, wherein weft fibers 112 run over and under adjacent warp fibers 114 in a repeating pattern. In general, any size of fiber 101 can be used and any degree of tightness in the weave can also be accommodated. Tighter weaves will tend to provide a smoother tissue-contacting surface while looser weaves will enhance the different levels of texture adding to the traction of the cover 50. Difference sizes of fibers 101 can occur in the same embodiment and different diameters of each fiber 101 can also offer different traction characteristics.

Figure 17:
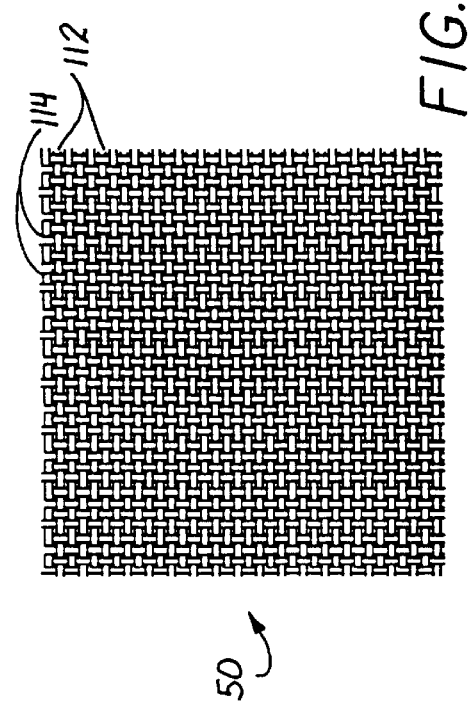
FIG. 17 illustrates a weave having more than one filament following the same path.
Figure 18:
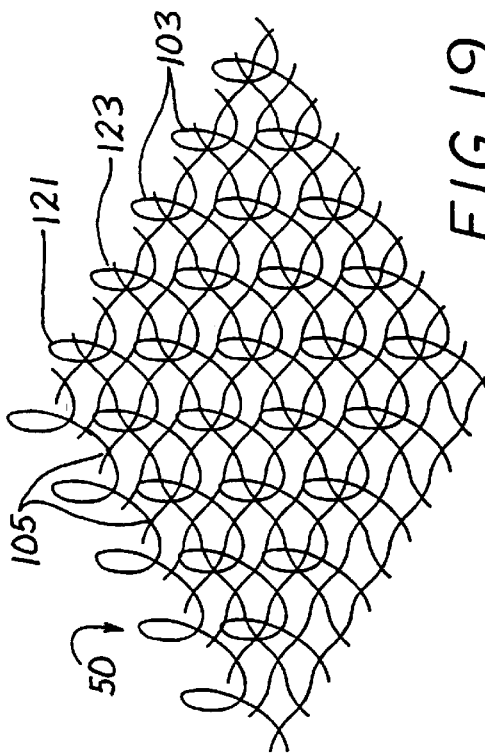
FIG. 18 is a top-plan view illustrating a weave with multiple sets of parallel filaments.
Figure 19:
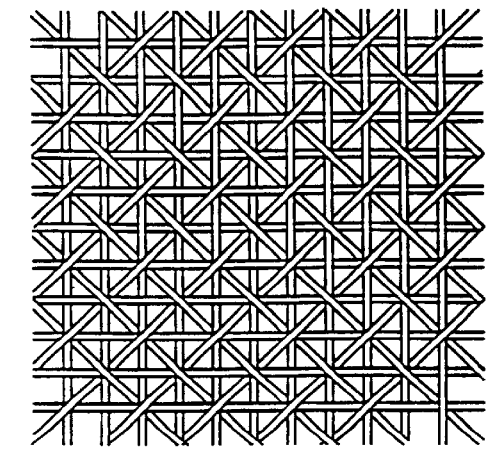
FIG. 19 illustrates a three-dimensional weave having discrete texture fibers.

As illustrated in FIG. 17, more than one of the fibers, such as those designated by the referenced numerals 116 and 118, may follow the same path in a particular weave. For example, there may be multiple sets of fibers with all of the fibers in each set extending in a common direction. Five sets of fibers are illustrated in the weave of FIG. 18. Other types of textures can be developed by lacing a conventional weave, such as that illustrated in FIG. 13, with individual "texture" fibers such as those designated by the reference numerals 121 and 123 in FIG. 19.

Having realized that it is the aggravated texture of the cover 50 which appears to add the highly desirable traction characteristics, it will now be appreciated that each of the fibers 101 can itself be provided with a surface characteristic which may be a particular advantage in different embodiments in the invention. Various fibers are illustrated in the perspective and cross-sectional views of FIGS. 20–26. A review of these figures will indicate that traction is affected not only by the texture associated with the woven or non-woven fabric, but also by the texture of each fiber which contributes to the fabric 106.

In the most elementary embodiments, the fiber 101, such as that illustrated in FIG. 20, will comprise a mono-filament 121 having a generally cylindrical configuration which in radial cross-section has the shape of a circle. The mono-filament 121 will typically have a smooth outer surface 123.

In the embodiment of FIG. 21, the fiber 101 is composed of a plurality of mono-filaments 125, which extend end-to-end throughout the fiber 101. More commonly, the multiple fibers 125 will be foreshortened, in which case they will be held together in the fiber 101 by entanglement and friction. In both of these multiple-filament embodiments, the filaments 125 can be tightly spun to form a thread, or more loosely spun to form a yarn.

The fiber 101 illustrated in FIG. 22 is representative of those embodiments having an outer surface 127 which is roughened, aggravated, uneven, unsmooth, or otherwise irregular. It should be understood that in general any texture applied to this outer surface 127 will enhance the traction of the associated fabric 106.

FIG. 23 illustrates a fiber 101, which is formed from sponge 130. The labyrinth of holes and tunnels formed in the sponge 130 will increase the traction of any fabric 106 made from this fiber 101, whether the sponge is rigid or soft.

The fiber 101 of FIG. 24 has a central channel 132 which provides the fiber 101 with a hollow configuration. This may be desirable in a particular embodiment, for example, if resilient characteristics are desired.

The fiber 101 illustrated in FIG. 25 has a polygonal cross-section, which is square in the illustrated embodiment. This cross-section for the fiber 101 forms ridges 134 along the fiber which can increase the traction of the associated fabric 106.

As illustrated in FIG. 26, the fiber 101 with a polygonal cross-section can be twisted so that the ridges 134 spiral around the fiber 101. This construction will also vary the traction of the associated fabric 106.

From these few examples of construction and materials, it can be seen that traction of the clamp 10 can be affected not only by the materials of the fibers 101, but also by the configuration of those materials. Other characteristics, such as absorption, can also be controlled at the fiber level.

Each of the fibers 101, or the associated fabric as a whole, can be coated with various materials desirable in a particular embodiment or surgical procedure. This coating, which may include either a solid or a liquid, might be applied with the intent to add something to the interface with the conduit 12, or to take something from the interface with the conduit 12. For example, the fibers 101 or fabric may be coated with a medicine to facilitate healing and reduce trauma. The coating 135 may also include a substance which would increase the coefficient of friction and the resulting traction with the conduit 12. The coating 135 may also include a hydrophylic material having characteristics for withdrawing moisture from the surface of the conduit 12.

It has been found that a drier interface between the clamp 10 and the conduit 12 will generally facilitate the desired traction. Broadly speaking, this drier interface between the clamp 10 and conduit 12 can be provided in three ways, each associated with the concept of the present invention. The first way to achieve a drier interface is to merely provide space into which moisture can flow in order to provide a more direct contact between the fibers 101 and the conduit 12. These spaces can be the interstices 110 of the fabric 106, or even the holes or channels associated with the fibers 101 of FIGS. 23 and 24. In a manner commonly associated with an automobile tire tread, these holes and channels provide space into which moisture can be displaced leaving a drier interface and thereby improving traction.

A second method for providing a drier interface is to form the fibers 101 and/or the fabric 106 loosely so that the surface tension of the filaments 125 and fibers 101 will draw moisture into the fabric 106.

A third method noted for providing a drier interface between the clamp 10 and conduit 12 is to form either the fabric 106 or the fibers 101 of a hydrophylic material or with a hydrophylic coating. This material can be relied on to draw moisture from the interface providing increased traction between the clamp 10 and conduit 12.

Certainly one of the purposes of the present invention is to provide increased traction between a clamp and a body conduit. This is accomplished in at least one embodiment by providing a multiplicity of fibers oriented to extend longitudinally between the clamp and the conduit. The fibers, which may themselves be composed of filaments, can be woven or non-woven into a fabric for covering a resilient pad or clamp insert. The fabric can be woven in any variety of weaves to provide the desired texture. The nature of the weave may control characteristics such as smoothness, absorption, and texture. The fibers and filaments may be formed from any solid or semi-solid material, each material adding its own characteristics to the resulting fabric, insert, or clamp. Within these broad general guidelines, many other structures and materials will be apparent to those skilled in the art.

It will be understood that many modifications can be made to the various disclosed embodiments without departing from the spirit and scope of the concept. For example, various sizes of the surgical device are contemplated as well as various types of constructions and materials. It will also be apparent that many modifications can be made to the configuration of parts as well as their interaction. For these reasons, the above description should not be construed as limiting the invention, but should be interpreted as merely exemplary of preferred embodiments. Those skilled in the art will envision other modifications within the scope and spirit of the present invention as defined by the following claims.

What is claimed is:

1. A surgical instrument for at least partially occluding a body conduit, comprising:
   a first jaw;
   a second jaw opposing the first jaw and movable relative to the first jaw to at least partially occlude the body conduit;
   a first layer carried by the first jaw and facing the second jaw, the first layer having first compliant characteristics and first absorption characteristics; and
   a second layer carried by the first jaw in juxtaposition to the first layer, the second layer having second compliant characteristics and second absorption characteristics, the second compliant characteristics of the second layer being less than the first compliant characteristics of the first layer, and the second absorption characteristics of the second layer being greater than the first absorption characteristics of the first layer.

2. The surgical instrument recited in claim 1, further comprising an insert having a substrate, the first layer and the second layer, wherein the first layer is disposed in contact with the substrate and the second layer.

3. The surgical instrument recited in claim 2, wherein the second layer comprises a fabric.

4. The surgical instrument recited in claim 3 wherein the fabric is woven.

5. The surgical instrument recited in claim 3, wherein the fabric is non-woven.

6. The surgical instrument recited in claim 3, wherein the fabric has properties that absorb fluids from the body conduit so as to enhance traction between the insert and the body conduit.

7. The surgical instrument recited in claim 3 wherein the fabric comprises a tube and at least the first layer of the insert is disposed in the tube.

8. The surgical instrument recited in claim 7 wherein the substrate of the insert is disposed in the tube.

9. The surgical instrument recited in claim 2, wherein the second layer comprises a multiplicity of fibers.

10. A surgical clamp for at least partially occluding a body conduit, comprising:
    a first jaw;
    a second jaw opposing the first jaw and movable relative to the first jaw to at least partially occlude the body conduit;
    a first layer carried by the first jaw and facing the second jaw, the first layer having first compliant characteristics and first absorption characteristics;
    a second layer carried by the first jaw in juxtaposition to the first layer, the second layer having second compliant characteristics and second absorption characteristics, the second compliant characteristics of the second layer being less than the first compliant characteristics of the first layer;
    the second absorption characteristics of the second layer being greater than the first absorption characteristics of the first layer; and
    a multiplicity of fibers included in the second layer and being oriented to extend generally in a common plane.

11. The surgical clamp recited in claim 10, wherein:
    the common plane is a first plane;
    the first jaw and the second jaw are oriented in a second plane; and the second plane of the jaws is generally perpendicular to the first plane of the fibers.

12. The surgical clamp recited in claim 11, wherein the multiplicity of fibers form a fabric.

13. The surgical clamp recited in claim 12, wherein the fabric is non-woven.

14. The surgical clamp recited in claim 12, wherein the fabric is woven.

15. The surgical clamp recited in claim 12, wherein the multiplicity of fibers further comprises:
- a first set of the fibers having a first orientation;
- a second set of the fibers having a second orientation; and
- the first orientation of the first fibers is different than the second orientation of the second fibers.

16. The surgical clamp recited in claim 15, wherein the first set of fibers and the second set of fibers intersect in a repetitive pattern.

17. The surgical clamp recited in claim 10, wherein:
- the fibers have a width;
- the second layer has a thickness; and
- the thickness of the second layer is not greater than two-times the width of the fibers.

18. The surgical clamp recited in claim 10, wherein the first layer and second layer form at least a portion of an insert removably attachable to the first jaw.

19. A surgical instrument for at least partially occluding a body conduit, comprising:
- a first jaw;
- a second jaw opposing the first jaw and movable relative to the first jaw to at least partially occlude the body conduit;
- an insert having a base;
- a first layer having first compliant characteristics and first absorption characteristics, the first layer being carried by the base and facing the second jaw;
- a second layer having second compliant characteristics and second absorption characteristics, the second compliant characteristics being less than the first compliant characteristics of the first layer, the second absorption characteristics being greater than the first absorption characteristics of the first layer, the second layer being carried by the first layer;
- a multiplicity of fibers included in the second layer, the fibers each having an elongate configuration and a side-surface extending longitudinally between a first end and a second end; and
- the side-surface of at least one of the fibers being uneven in order to provide the second layer with improved traction relative to the body conduit.

20. The surgical clamp recited in claim 19, wherein the uneven surface has peaks and valleys which provide the surface with a roughened texture.

21. The surgical clamp recited in claim 19, wherein the uneven surface comprises a ridge extending at least partially between the first end and second end of the fiber.

22. The surgical clamp recited in claim 21, wherein the fiber is twisted so that the ridge spirals around the surface.

23. The surgical clamp recited in claim 19, wherein the fibers are hollow.

24. The surgical clamp recited in claim 19, wherein the multiplicity of fibers form a fabric having characteristics for absorbing fluids.

25. The surgical clamp recited in claim 24, wherein at least one of the fibers has characteristics for absorbing fluids.

26. The surgical clamp recited in claim 19, wherein the second layer has a first area of contact with the body conduit when the clamp initially contacts the body conduit, and a second area of contact greater than the first area of contact when the clamp at least partially occludes the body conduit.

27. A surgical clamp for at least partially occluding a body conduit, comprising:
- a first jaw;
- a second jaw opposing the first jaw and movable relative to the first jaw to at least partially occlude the body conduit; and
- an insert carried by the first jaw and facing the second jaw, the insert having a first layer and a second layer in juxtaposition to the first layer, the first layer having first compliant characteristics and first absorption characteristics, the second layer having second compliant characteristics and second absorption characteristics, the second compliant characteristics of the second layer being less than the first compliant characteristics of the first layer, and the second absorption characteristics of the second layer being greater than the first absorption characteristics of the first layer.

28. The surgical clamp recited in claim 27, wherein the second layer of the insert comprises a multiplicity of fibers forming a fabric.

29. The surgical clamp recited in claim 28, wherein the fibers are arranged in a random orientation.

30. The surgical clamp recited in claim 28, wherein the fibers form a woven fabric.

31. The surgical clamp recited in claim 30, wherein the fabric is woven in a three-dimensional weave.

32. The surgical clamp recited in claim 30, wherein the fabric is woven with more than one of the fibers following the same path in the fabric.

33. The surgical clamp recited in claim 28, wherein the fibers form a non-woven fabric.

34. A surgical clamp for at least partially occluding a body conduit, comprising:
- a first jaw;
- a second jaw opposing the first jaw and movable relative to the first jaw to at least partially occlude the body conduit;
- a first layer carried by the first jaw and facing the second jaw, the first layer having first compliant characteristics and first absorption characteristics;
- a second layer carried by the first jaw in juxtaposition to the first layer, the second layer having second compliant characteristics and second absorption characteristics;
- the second compliant characteristics of the second layer being less than the first compliant characteristics of the first layer;
- the second absorption characteristics of the second layer being greater than the first absorption characteristics of the first layer;
- a multiplicity of hollow fibers included in the second layer, the fibers having an elongate configuration and having a side-surface extending longitudinally between a first end and a second end; and
- the side-surface of at least one of the fibers being uneven in order to provide the second layer with improved traction relative to the body conduit.

* * * * *